United States Patent
Weber et al.

(10) Patent No.: US 7,074,202 B1
(45) Date of Patent: Jul. 11, 2006

(54) ARM BRACE APPARATUS WITH PRE-POSITIONING MEANS

(75) Inventors: James J. Weber, Santa Barbara, CA (US); David Auerbach, Calabasas, CA (US)

(73) Assignee: Weber Orthopedic Inc., Santa Paula, CA (US)

( * ) Notice: Subject to any disclaimer, the term of this patent is extended or adjusted under 35 U.S.C. 154(b) by 0 days.

(21) Appl. No.: 10/928,972

(22) Filed: Aug. 30, 2004

(51) Int. Cl.
*A61F 5/00* (2006.01)

(52) U.S. Cl. .............................. 602/20; 602/5; 602/62; 128/878

(58) Field of Classification Search .................... 602/5, 602/6, 20, 21, 22, 62; 128/878, 881; 2/16
See application file for complete search history.

(56) References Cited

U.S. PATENT DOCUMENTS

| | | | | |
|---|---|---|---|---|
| 1,431,915 A * | 10/1922 | De Barr | ...................... | 128/881 |
| 2,468,580 A * | 4/1949 | Weis et al. | .................. | 473/214 |
| 2,703,082 A * | 3/1955 | Emert | ......................... | 128/881 |
| 3,785,371 A * | 1/1974 | Lewis | ......................... | 602/20 |
| 3,990,709 A * | 11/1976 | DeRogatis | .................. | 473/214 |
| 4,048,674 A * | 9/1977 | Chesnick | .......................... | 2/16 |
| 4,875,677 A * | 10/1989 | Tetreault | ..................... | 473/458 |
| 5,048,837 A * | 9/1991 | Manley et al. | .............. | 473/214 |
| 5,248,292 A * | 9/1993 | Holland | ......................... | 602/6 |
| 5,591,121 A * | 1/1997 | Cantrell | ......................... | 602/5 |
| 5,662,595 A * | 9/1997 | Chesher et al. | ............... | 602/20 |
| 5,715,535 A * | 2/1998 | Hamilton et al. | ................ | 2/59 |
| 5,873,847 A * | 2/1999 | Bennett et al. | ............... | 602/16 |
| 6,000,402 A * | 12/1999 | Able | .......................... | 128/869 |
| 6,179,799 B1 * | 1/2001 | Doran | ......................... | 602/20 |
| 6,245,034 B1 * | 6/2001 | Bennett et al. | ............... | 602/20 |
| 6,322,462 B1 * | 11/2001 | Kafer | ......................... | 473/458 |
| 6,730,052 B1 * | 5/2004 | Chow | ........................... | 602/20 |
| 2004/0153016 A1 * | 8/2004 | Salmon et al. | ................ | 602/16 |

* cited by examiner

*Primary Examiner*—Henry Bennett
*Assistant Examiner*—Amanda Wieker
(74) *Attorney, Agent, or Firm*—William W. Haefliger

(57) ABSTRACT

An arm brace comprising an elongated relatively stiff support configured for application adjacent the inner side of the arm and for nesting adjacent the obtusely angled inner side zone of the partly bent arm opposite the elbow; retainer straps carried by the support near opposite ends thereof, to be independently tightened about the arm at retention locations spaced from a shallow angle shaped mid-section of the support, whereby the user's arm is maintained in shallowly bent condition by the brace.

14 Claims, 4 Drawing Sheets

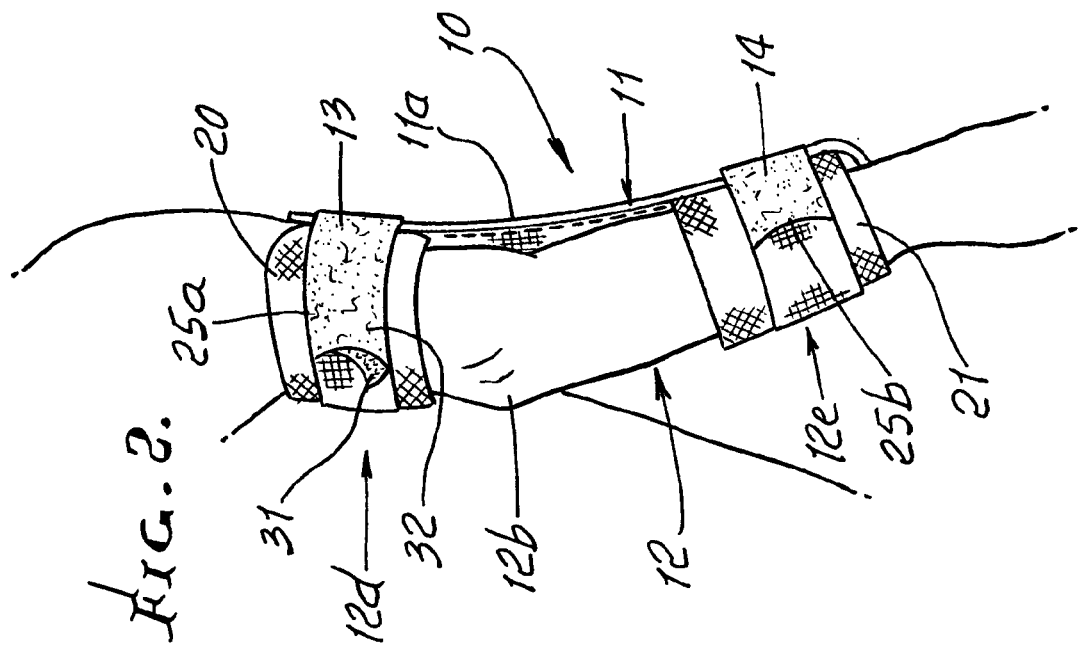
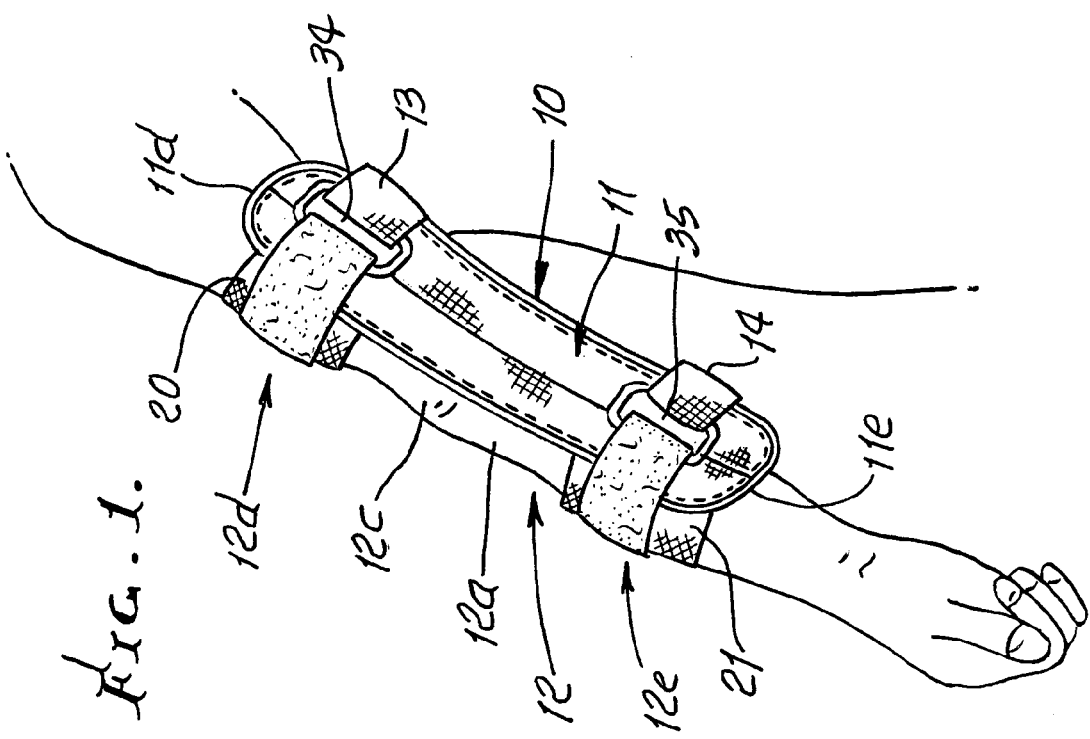

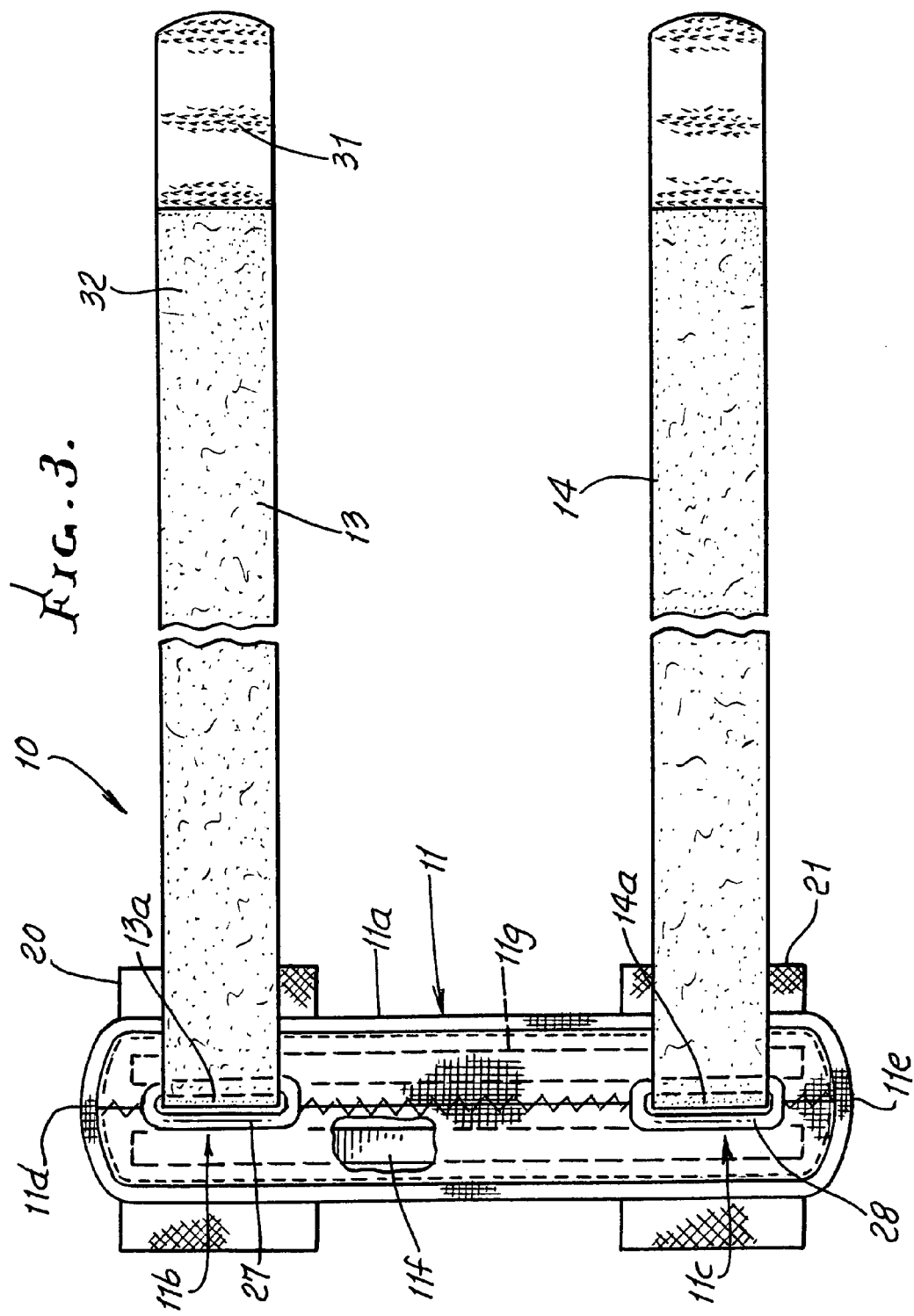

ARM BRACE APPARATUS WITH PRE-POSITIONING MEANS

BACKGROUND OF THE INVENTION

This invention relates generally to therapeutic arm support apparatus or braces, and more particularly to improvements in braces adapted to hold the arm in a predetermined, comfortable, partly bent position, as during rest.

There is constant need for improvements in such braces, facilitating ease of application to the arm, ease of connection to the arm, the brace configured in a non-bulky form. These functions are desirably to be realized when the user uses his other arm in a "one-handed" way, to apply the brace.

SUMMARY OF THE INVENTION

It is a major object of the invention to provide an improved arm brace apparatus, meeting the above needs. Basically the bent mode brace includes a) an elongated relatively stiff support configured for application adjacent the inner side of the arm and for nesting at the inner curved side of the partly bent arm opposite the elbow, b) retainer straps carried by the support near opposite ends thereof, to be independently tightened about the arm at locations everywhere spaced from a shallow arch shaped mid-section of the support, c) whereby the user's arm is maintained in partly bent condition by the brace.

As will be seen, the support has opposite, substantially flat sides about which said straps extend; and hook and pile connection may be provided on the straps, for rapid and efficient application to the brace to the inner side of the arm. Such application is initially aided by provision of a flexible sleeve or sleeves carried by the support to receive the user's arm at the outer side of the support. Each sleeve typically has opposite ends connected to said outer side of the support, each sleeve being resiliently stretchable; and the sleeves may be protectively located proximate the traps, i.e. at strap tightening locations, so that the sleeves and straps cooperate in locating the support relative to the use's arm during the two-step strap connection process.

Further objects include provision of the support to include:

i) at least one elongated metallic stiffener, ii) jacketing material covering said stiffener, said jacketing including cushioning means.

Cushioning means may be provided at opposite sides of the support, and at support edges.

The method of use of the support includes:

i) applying the brace to the inner curved side of the partly bent arm, without first fastening the brace to the arm by the straps, ii) initially retaining the brace to the arm, iii) and then manipulating the straps to tighten the brace to the arm at locations spaced from the shallow arch mid-section of the support.

In this regard, the method may include provision of a flexible sleeve or sleeves to be carried by the support, and to extend at the outer side of the support, the user's arm being received through the sleeve or sleeves, on initial retention of the brace to the arm.

As will be seen, the flexible sleeves act to initially position the brace in nesting relation to the partly bent arm, to enable the straps to then be tightened without the brace slipping out of position as during such tightening.

These and other objects and advantages of the invention, as well as the details of an illustrative embodiment, will be more fully understood from the following specification and drawings, in which:

DRAWING DESCRIPTION

FIG. 1 is a perspective view showing use of the arm brace of the invention, at one side of the brace;

FIG. 2 is another perspective view showing use of the arm brace of the invention, at another side of the brace;

FIG. 3 is an enlarged view showing the inner side of the brace, with two straps extended;

DETAILED DESCRIPTION

Figure 4:
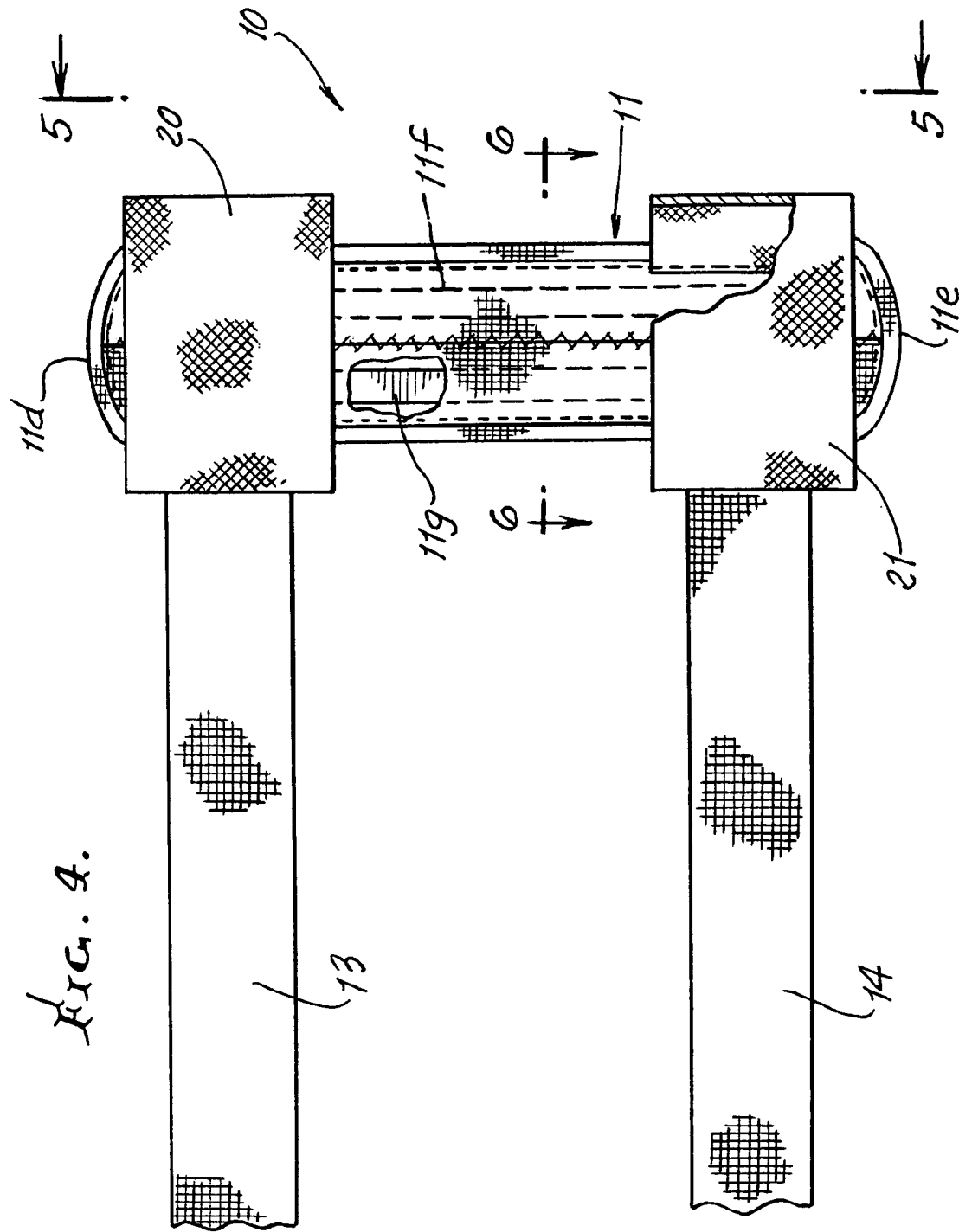
FIG. 4 is an enlarged view showing the outer side of the brace, with the two straps extended.

Referring first to FIGS. 1 and 2, showing a preferred form of the invention, the arm brace 10 includes:

a) an elongated, relatively stiff support 11 configured for application against or adjacent the inner side 12a of the user's arm 12 above and below the elbow 12b, and having shallow angularity for nesting of a mid-portion 11a of the support at or adjacent the obtusely angled inner side zone 12c of the partly bent arm opposite the elbow 12b, b) retainer straps 13 and 14 carried by the support at endwise opposite locations 11b and 11c between mid-portion 11a and support ends 11d and 11e, to be independently tightened about the arm at retention locations 12d and 12e spaced from shallow angled mid-portion 11a of the support, c) whereby the user's arm is maintained in partly bent relatively comfortable condition by the brace, for example allowing sleeping with low level discomfort.

Figure 6:
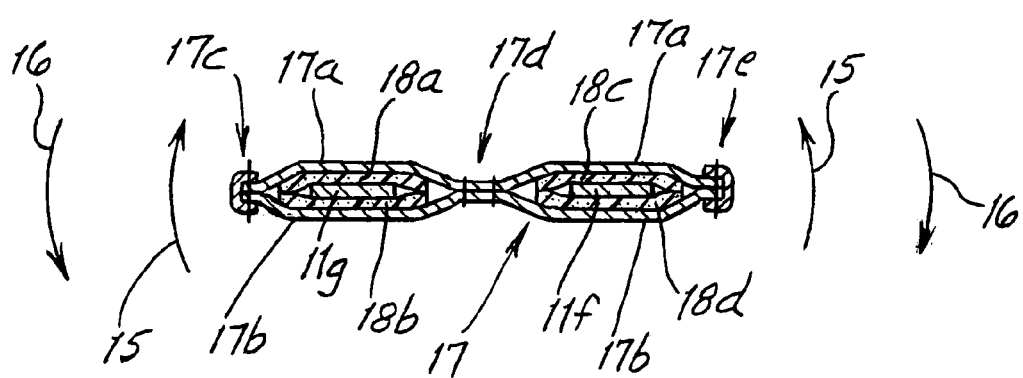
FIG. 6 is an enlarged section taken on lines 6—6 of FIG. 4.

The support 11 may consist of at least one layer or strips of lightweight metal, such as aluminum, allowing forcible adjustment of the degree of shallow angled bending of the support, at mid-portion 11a. The support layer thickness may for example be between about $\frac{1}{16}$ inch and $\frac{3}{16}$ inch; and it typically has convex edges at its opposite ends 11d and 11e. As shown in FIGS. 3, 4 and 6, the support consists of two parallel, elongated layers or strips 11f and 11g which are spaced apart to allow limited transverse flexing as in directions 15 and 16, in FIG. 6 to accommodate to arm transverse curvature. Accommodative non-metallic jackets or sleeve material 17, extend at jacket zones 17a and 17b at opposite sides of the layers. Sleeve material is interconnected at transverse locations 17c, 17d, and 17e. Cushioning is provided at 18a, 18b, 18c and 18d, at opposite sides of the straps and layers, and retained by the jacketing 17. Support layers 11f and 11g act as elongated stiffeners, within the jacketing.

A flexible sleeve or sleeves is or are carried by the support to receive the user's arm at the outer side of the support. See for example the two sleeves or bands 20 and 21, made of flexible fabric, which may be resiliently stretchable, and having end portions 20a and 21a connected to the support as at 22 and 23, in spaced relation to the support mid-portion 11a. The sleeves initially hold the support for positioning adjustment to the user's one arm, freeing the user's other arm for use in tightening straps 13 and 14 for firmly holding the support to the arm as seen in FIGS. 1 and 2. Also, the sleeves are preferably located proximate the strap wraparound positions, to cooperate with the straps during complete connection to the user's arm, the sleeves being wider than the straps, to assure strap engagement with the sleeves during tightening. As thus located, the sleeves also act as buffers or cushions between the user's arm and the straps, during strap tightening, enhancing comfort. Accordingly, the sleeves have multiple functions, and essential simplicity in use and application of the apparatus are maintained.

Figure 5:
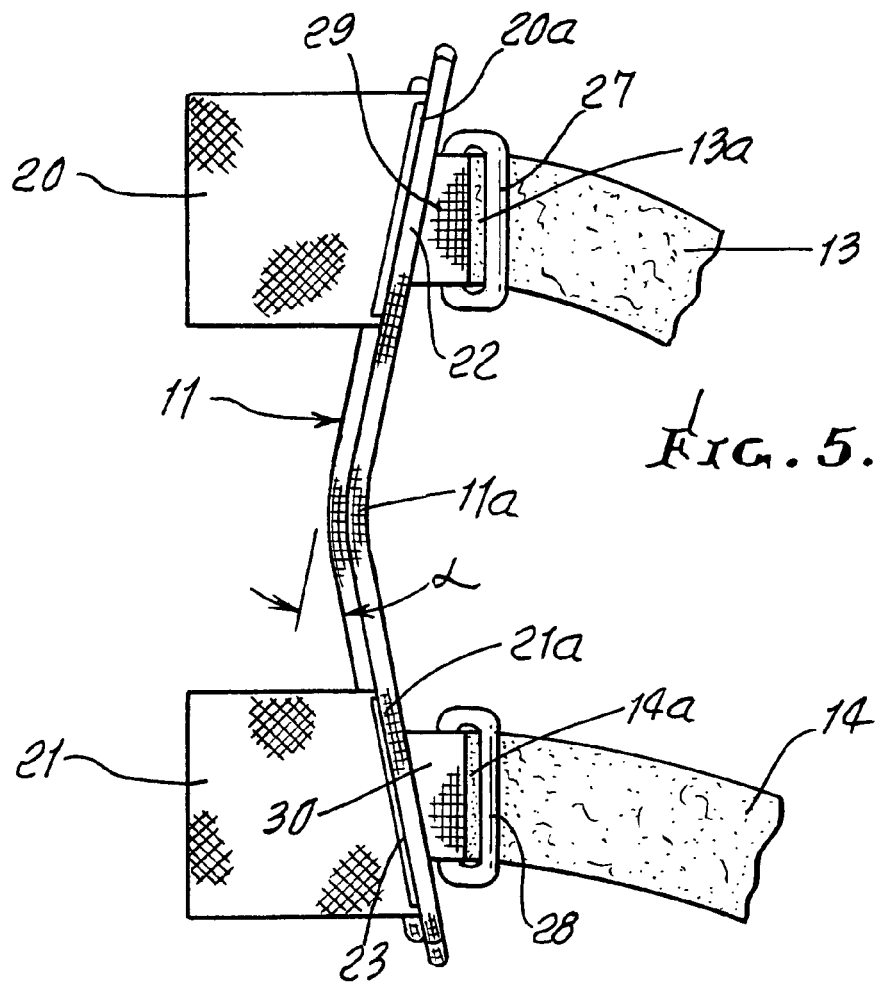
FIG. 5 is an edge view of the brace, taken on lines 5—5 of FIG. 4 showing its angularity, with straps extended.

The retainer straps 13 and 14 have end portions 13a and 14a attached to the support, as via buckle type loops 27 and 28, best seen in FIG. 5. The loops are attached to the support as via holders 29 and 30. The elongated straps may carry hook and pile material, indicated at 31 and 32, to be adjustably pressed and locked together, in the strap tightened positions as seen in FIGS. 1 and 2. The free ends 25a and 25b of the straps fit under retention bands 34 and 35 carried by the loops 25 and 26.

The apparatus as described can be easily affixed to the arm, by
- i) applying the brace to the inner curved side of the partly bent arm, without first fastening the brace to the arm by said straps,
- ii) initially retaining the brace to the arm,
- iii) and then manipulating said straps to tighten the brace to the arm at locations spaced from the shallow arch mid-section of the support.

Such tightening is aided by providing a flexible sleeve or sleeves to be carried by the support, and to extend at the outer side of the support, the user's arm being received through sleeve or sleeves, for said initial retaining of the brace to the arm.

The support 10 may consist of one unitary piece of the same relatively stiff material, and/or curved as shown, and to which a looping retention band, or bands, may be applied, to extend about the user's arm; and to which a retention strap or straps may then be applied, to extend about the user's arm. The support or brace has width between 2 and 3½ inches, and length between 10½ and 14½ inches. Angularity α as between support portions extending away from the mid-section is between 10° and 30°. That mid-section 11a may be arching, as shown.

It will be noted that each arm band has width substantially exceeding the width of the strap located proximate that arm band. This assures strap engagement with the arm band and not the user's bare arm.

We claim:

1. An arm brace comprising:
   a) an elongated relatively stiff support configured for application adjacent the inner side of the arm and for nesting adjacent the obtusely angled inner side zone of the partly bent arm opposite the elbow,
   b) retainer straps carried by the support near opposite ends thereof, to be independently tightened about the arm at retention locations spaced from a shallow angle shaped mid-section of the support,
   c) whereby the user's arm is maintained in shallowly bent condition by the brace,
   d) and including flexible arm bands carried by the support to receive and position the user's arm at the outer side of the support, and wherein each arm band extends in a loop projecting away from the support and has opposite ends connected to said outer side of the support, thereby to define a continuous loop completely surrounding the arm, in use, each arm band being resiliently stretchable, and wherein the arm bands are located proximate the straps, to cooperate therewith during complete connection to the user's arm.

2. The arm brace of claim 1 wherein the support has opposite, substantially flat sides about which said straps extend.

3. The arm brace of claim 1 including hook and pile connections on said straps.

4. The arm brace of claim 1 wherein the support includes:
   i) at least one elongated metallic stiffener,
   ii) jacketing material covering said stiffener, said jacketing including cushioning means.

5. The arm brace of claim 1 wherein the support includes
   i) at least one elongated metallic stiffener,
   ii) jacketing material covering said stiffener, said jacketing including cushioning means,
   iii) said cushioning means located at opposite sides of the support, and at edges of the support.

6. The arm brace of claim 1, the support having a mid-section defining a shallow arch, and two elongated sections projecting oppositely from said mid-section, the straps carried by said two elongated sections.

7. The method of use of the arm brace of claim 1 which includes:
   i) applying the brace to the inner curved side of the partly bent arm, without first fastening the brace to the arm by said straps,
   ii) initially retaining the brace to the arm, by providing said arm bands in configuration for receiving the user's arm through the arm bands,
   iii) and then manipulating said straps to tighten the brace to the arm at locations spaced from said shallow mid-section of the support, which is arched.

8. The method of claim 7 wherein the arm bands are provided to be carried by the support, and to openly project away from the outer side of the support, to enable the user's arm to be received through said arm bands, on said initial retaining of the brace to the arm.

9. The method of claim 8 wherein the straps are sufficiently tightened to hold the user's arm against flexing.

10. The arm brace of claim 1 wherein the support includes at least two, spaced, parallel, elongated, metallic stiffener layers, which have limited bendabilty.

11. The arm brace of claim 1 wherein each arm band has width substantially exceeding the width of the strap located proximate that arm strap.

12. For use in an arm brace, apparatus comprising
   a) an elongated relatively stiff support sized to be positioned adjacent the inner side of the user's arm and lengthwise thereof,
   b) said support having a mid-portion which is angled to nest at the user's bent arm extent opposite the elbow,
   c) and means for retaining the support to the arm at locations spaced from said support mid-portion, said means including flexible arm bands carried by the support to receive and position the user's arm at the outer side of the support, and wherein each arm band extends in a loop projecting away from the support and has opposite end extents connected to said outer side of the support, thereby to define a continuous loop completely surrounding the arm, in use, each arm band being resiliently stretchable, and wherein the arm bands are located proximate retainer straps, to cooperate therewith during complete connection to the user's arm.

13. Apparatus as defined in claim 12 wherein said support arches at said mid-portion, and having width between 2 and 3½ inches, and length between 10½ and 14½ inches.

14. The apparatus of claim 12 wherein said mid-portion is angled at between 10° and 30°.

* * * * *